United States Patent
Berthon-Jones et al.

(10) Patent No.: US 7,988,640 B2
(45) Date of Patent: Aug. 2, 2011

(54) MACRO-CONTROL OF TREATMENT FOR SLEEP DISORDERED BREATHING

(75) Inventors: Michael Berthon-Jones, Leonay (AU); Gordon Joseph Malouf, Elizabeth Bay (AU); Peter Edward Bateman, Cherrybrook (AU); David John Bassin, Coogee (AU); Robert Henry Frater, Lindfield (AU); Steven Paul Farrugia, Lugamo (AU)

(73) Assignee: Resmed Limited, New South Wales (AU)

( * ) Notice: Subject to any disclaimer, the term of this patent is extended or adjusted under 35 U.S.C. 154(b) by 1315 days.

(21) Appl. No.: 10/595,917

(22) PCT Filed: Nov. 25, 2004

(86) PCT No.: PCT/AU2004/001652
§ 371 (c)(1),
(2), (4) Date: Jun. 12, 2006

(87) PCT Pub. No.: WO2005/051470
PCT Pub. Date: Jun. 9, 2005

(65) Prior Publication Data
US 2007/0142741 A1    Jun. 21, 2007

(51) Int. Cl.
*A61B 5/08*    (2006.01)
(52) U.S. Cl. .................................................. 600/532
(58) Field of Classification Search .......... 600/529–543; 128/200.24
See application file for complete search history.

(56) References Cited

U.S. PATENT DOCUMENTS

| | | | |
|---|---|---|---|
| 4,944,310 | A | 7/1990 | Sullivan |
| 5,134,995 | A | 8/1992 | Gruenke et al. |
| 5,199,424 | A | 4/1993 | Sullivan et al. |
| 5,203,343 | A | 4/1993 | Axe et al. |
| 5,245,995 | A | 9/1993 | Sullivan et al. |
| 5,335,654 | A | 8/1994 | Rapoport |
| 5,458,137 | A * | 10/1995 | Axe et al. ............... 128/204.23 |
| 5,704,345 | A | 1/1998 | Berthon-Jones |
| 5,823,187 | A | 10/1998 | Estes et al. |
| 5,937,853 | A | 8/1999 | Strom |
| 6,367,474 | B1 | 4/2002 | Berthon-Jones et al. |

(Continued)

FOREIGN PATENT DOCUMENTS

EP    788805    8/1997

(Continued)

OTHER PUBLICATIONS

Notice of Reasons for Rejection, Japanese Patent Office, Application No. P2006-540093, Apr. 27, 2010.

(Continued)

*Primary Examiner* — Charles A Marmor, II
*Assistant Examiner* — Karen E Toth
(74) *Attorney, Agent, or Firm* — Gottlieb Rackman & Reisman, PC (57) ABSTRACT

A method and apparatus for treating sleep disordered breathing. An arousal index is determined for use in an outer loop of a control algorithm, the arousal index being a measure of the frequency of sleep arousals. The respiratory airflow signal in an inner loop of the control algorithm is monitored to detect an airway obstruction. If the arousal index is high, then the sensitivity of obstruction detection and/or the aggressiveness of the treatment is increased, and if the arousal index is low, then the sensitivity of the obstruction detection and/or the aggressiveness of the treatment is decreased.

16 Claims, 8 Drawing Sheets

U.S. PATENT DOCUMENTS

| | | | |
|---|---|---|---|
| 6,532,959 | B1 | 3/2003 | Berthon-Jones |
| 6,814,073 | B2 | 11/2004 | Wickham |
| 2003/0062044 | A1 | 4/2003 | Berthon-Jones et al. |
| 2003/0121519 | A1 | 7/2003 | Estes et al. |
| 2005/0076908 | A1* | 4/2005 | Lee et al. ............. 128/204.23 |
| 2005/0115561 | A1* | 6/2005 | Stahmann et al. ....... 128/200.24 |
| 2007/0084464 | A1* | 4/2007 | Wickham et al. ........ 128/204.23 |
| 2010/0076333 | A9* | 3/2010 | Burton et al. ................ 600/544 |

FOREIGN PATENT DOCUMENTS

| | | |
|---|---|---|
| JP | 2001-000547 | 1/2001 |
| WO | 92-22244 | 12/1992 |
| WO | 97-16216 | 5/1997 |
| WO | 03-030804 | 4/2003 |

OTHER PUBLICATIONS

Ayappa I, Norman R, et al. Non-invasive detection of respiratory effort related arousals by a nasal cannula/pressure transducer system Sleep 2000, 23:763-771.

Hosselet J, Ayappa I, et al. Classification of sleep disordered breathing. American journal of respiratory and critical care medicine 2001, 163:398-405.

* cited by examiner

MACRO-CONTROL OF TREATMENT FOR SLEEP DISORDERED BREATHING

FIELD OF THE INVENTION

This invention relates to methods and apparatus for treating sleep disordered breathing. In particular, the invention relates to automatic adjustment of control parameters for apparatus used in the treatment of sleep disordered breathing.

BACKGROUND OF THE INVENTION

Sullivan invented the treatment of Obstructive Sleep Apnea (OSA) with nasal Continuous Positive Airway Pressure (CPAP). (See U.S. Pat. No. 4,944,310.) Diagnosis of OSA typically requires two nights in a sleep clinic. During a first night, the patient is monitored to see whether the patient has OSA. During the second night, a range of nasal mask pressures are tested to determine an appropriate pressure setting for a CPAP device to keep the patient's airway open. Once a pressure setting is determined, the patient is prescribed a CPAP device set to that pressure for subsequent home treatment. Because of limited places in sleep clinics, a patient can wait up to two years before he has the opportunity to be diagnosed. More recently, automatic devices have been developed which can diagnose and treat patients in their own homes, reducing the delay. Some automatic devices also can increase and decrease the treatment pressure during the night in accordance with patient need.

U.S. Pat. No. 5,199,424 (Sullivan and Lynch) describes a device for monitoring breathing during sleep and control of CPAP treatment that is patient controlled. In particular, the patent describes a CPAP apparatus including a controllable variable-pressure air source; a nose piece for sealed air communication with a patient's respiratory system; an air communication line from the air source to the nose piece; a sound transducer adapted to be in sound communication with the patient's respiratory system; and a feedback system controlling the output pressure of the air source in response to an output from the transducer so as to increase the pressure of the air source, in response to detection of sound indicative of snoring, in accordance with a predefined procedure. The sound transducer, in its most general form, comprises a pressure transducer which, in addition to detecting snoring sounds, can detect other respiratory parameters such as the rate of breathing, inhaled air flow volume, and inhaled air flow rate. The output air pressure of the air source is increased in response to one or more of these parameters in accordance with a pre-defined procedure.

U.S. Pat. No. 5,134,995 (Gruenke et al.) is said to describe an apparatus and method for facilitating the respiration of a patient for treating mixed and obstructive sleep apnea and certain cardiovascular conditions, among others, by increasing nasal air pressure delivered to the patient's respiratory passages just prior to inhalation and by subsequently decreasing the pressure to ease exhalation effort. The preferred apparatus includes a patient-coupled air delivery device for pressurizing the patient's nasal passages at a controllable pressure, and a controller coupled with the delivery device having a pressure transducer for monitoring the nasal pressure and a micro-controller for selectively controlling the nasal pressure. In operation, the controller determines a point in the patient's breathing cycle just prior to inhalation and initiates an increase in nasal pressure at that point in order to stimulate normal inhalation, and subsequently lowers the nasal pressure to ease exhalation efforts.

U.S. Pat. No. 5,203,343 (Axe et al.) is said to describe a method and device for controlling sleep disordered breathing utilizing variable pressure. A compressor supplies air at a relatively low pressure to the user's air passages while the user is asleep. A pressure transducer monitors the pressure and converts the pressure to an electrical signal. The electrical signal is filtered and compared with the characteristics of waveforms that exist during snoring. If the envelope of the waveform exceeds an average threshold value in duration and in area, then a microprocessor treats the envelope as possibly being associated with a snore. If a selected number of envelopes of this nature occur within a selected time period, then the microprocessor considers snoring to exist and increases the pressure of the compressor. If snoring is not detected within a certain time period, then the microprocessor lowers the level gradually.

U.S. Pat. No. 5,335,654 (Rapoport) is said to describe, in the treatment of obstructive sleep apnea, a CPAP flow generator employed to direct air to a nasal mask fitted to a patient. The airflow from the generator is monitored, and the flow and/or pressure is increased when the waveform of the airflow exhibits characteristics corresponding to flow limitation. The generator may be controlled to repetitively test for waveform variations, in order to adjust the CPAP flow to the minimum level that does not produce flow limitation.

U.S. Pat. No. 5,704,345 (Berthon-Jones) describes a method and apparatus for detection of apnea and obstruction of the airway in the respiratory system. Methods and apparatus for determining the occurrence of an apnea, patency and/or partial obstruction of the airway are disclosed. Respiratory air flow from a patient is measured to provide an air flow signal. The determination of an apnea is performed by calculating the variance of the air flow signal over a moving time window and comparing the variance with a threshold value. One determination of partial obstruction of the airway is performed by detecting the inspiratory part of the air flow signal, scaling it to unity duration and area, and calculating an index value of the amplitude of the scaled signal over a mid-portion. Alternatively, the index value is a measure of the flatness of the air flow signal over the mid-portion. One determination of patency of the airway is performed by applying an oscillatory pressure waveform of known frequency to a patient's airway, calculating the magnitude of the component of the air flow signal at the known frequency induced by the oscillatory pressure waveform, and comparing the calculated magnitude with a threshold value. Alternatively, the air flow signal is analyzed to detect the presence of a component due to cardiogenic activity.

U.S. Pat. No. 6,367,474 (Berthon-Jones and Farrugia) describes CPAP treatment apparatus having a controllable flow generator operable to produce breathable air to a patient at a treatment pressure elevated above atmosphere by a delivery tube coupled to a mask having a connection with a patient's airway. A sensor generates a signal representative of patient respiratory flow that is provided to a controller. The controller is operable to determine the occurrence of an apnea from a reduction in respiratory airflow below a threshold and, if an apnea has occurred, to determine the duration of the apnea and to cause the flow generator to increase the treatment pressure by an amount which is an increasing function of the duration of the apnea, and a decreasing function of the treatment pressure immediately before the apnea.

In general, these types of techniques of control of the administration of CPAP treatment can be regarded as "micro-control" algorithms. That is, they monitor the condition of the patient at any given moment. A variety of techniques for monitoring the patient's condition may be used, including detecting flattening of the inspiratory flow-time curve, detecting a reduction in patient ventilation, and detecting snoring. If there is an indication of sleep disordered breathing, the response is to increase the treatment pressure. Absent the indication of sleep disordered breathing, treatment pressure may be decreased. A question of interest is how effective such algorithms are in treating OSA.

The Apnea-Hypopnea Index (AHI) provides a measure of the number of apneas and hypopneas which a patient experiences during sleep. The AHI is sometimes used to assist in diagnosis of OSA. The AHI may also be used as an indication of the effectiveness of the nasal CPAP treatment. Hence, at least one automatic CPAP device, the AUTOSET T™, manufactured by ResMed Limited, reports the AHI, among other things, after a night's treatment. A problem with such an approach is that if the AHI indicates that therapy has been ineffective, the device may not be able to respond to such a result without being adjusted by a technician or clinician.

BRIEF DESCRIPTION OF THE INVENTION

In accordance with a first aspect of the invention a method and apparatus for treating sleep disordered breathing is provided that automatically adjusts its sensitivity to indications of sleep disordered breathing.

In accordance with another aspect of the invention, a method and apparatus for treating sleep disordered breathing is provided that monitors a patient's sleep arousal and in accordance with a measure of sleep arousal automatically adjusts how aggressively it responds to indications of sleep disordered breathing.

In accordance with another aspect of the invention, a method and apparatus for treating sleep disordered breathing is provided in which the effectiveness of therapy is continuously monitored. Where there is an indication that therapy has not been effective, treatment pressure changes are accelerated. Where there is an indication that therapy has been effective, treatment pressure changes are decelerated.

In accordance with another aspect of the invention, in methods and apparatus providing micro-control of sleep disordered breathing, a macro-control algorithm is provided that monitors its effectiveness and adjusts its operational parameters if they prove ineffective. Thus, a first detection control loop detects the effectiveness of a second detection control loop by examining the changing condition of the patient, and then the first detection control loop adjusts the second detection control loop to improve performance of the first control loop.

In accordance with another aspect of the invention, in methods and apparatus for providing treatment of sleep disordered breathing, an arousal index is determined for use in an outer loop of a control algorithm, the arousal index being a measure of the frequency of sleep arousals. A respiratory airflow signal of the patient is monitored in an inner loop of the control algorithm to detect obstructions. If the arousal index is high, then the sensitivity of obstruction detection and/or the aggressiveness of the treatment is increased, and if the arousal index is low, then the sensitivity of the obstruction detection and/or the aggressiveness of the treatment is decreased.

In accordance with another aspect of the invention there are provided methods and apparatus for treating sleep disordered breathing having an inner control loop and an outer control loop wherein the inner loop is adapted to provide at least two treatment modes and the outer loop is adapted to monitor the effectiveness of therapy provided by the inner loop and change modes if necessary.

In accordance with another aspect of the invention there is provided a controller for a device for treating sleep disordered breathing, the controller programmed to provide a set of alternative treatment algorithms and programmed to select the most appropriate member of the set in accordance with indications of sleep disordered breathing.

DETAILED DESCRIPTION OF THE INVENTION

Figure 1:
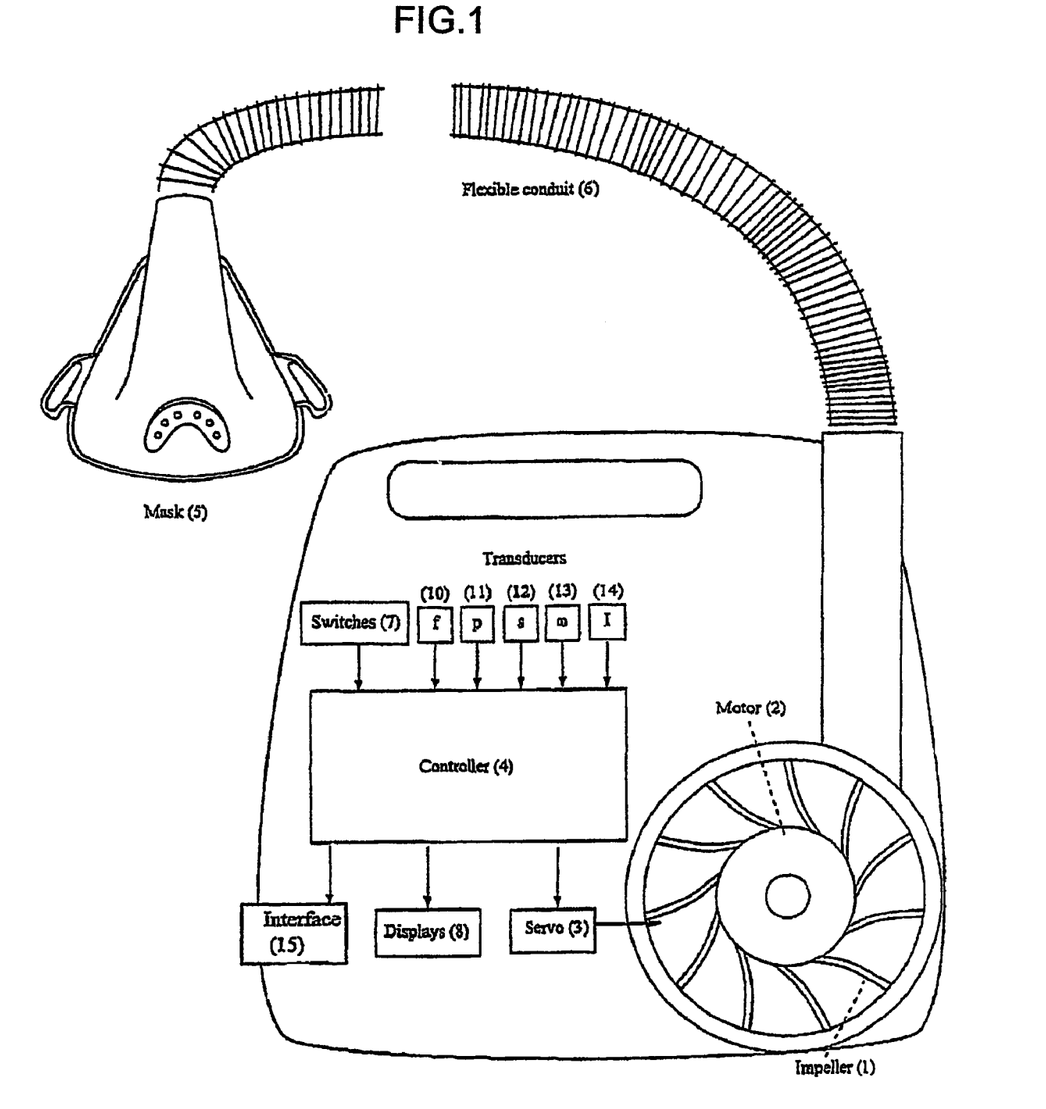
FIG. 1 shows an apparatus in accordance with the invention.

Apparatus suitable for performing the invention is shown in FIG. 1. An impeller 1 is coupled to an electric motor 2 which is connected to a servo 3 and directed by a controller 4. The controller 4 includes a microprocessor, data storage, and memory programmed with algorithms in accordance with the invention. Thus, the controller or processor is configured and adapted to implement the methodology described in more detail herein and may include integrated chips, a memory and/or other instruction or data storage medium. Programmed instructions either may be coded on integrated chips in the memory of the device or may be loaded as software.

The impeller, motor and controller assembly form the blower. A mask 5 is connected to the blower via a flexible conduit 6. Various switches 7 and displays 8 are provided on the housing of the blower. A number of sensors are provided within the blower to monitor, among other things, flow 10, pressure 11, snore 12, motor speed 13 and motor current 14. Various devices are known in the art that can serve as these types of sensors. A communications interface 15 is provided which allows data to be transferred between the apparatus and an external device, such as a computer or controller. While in a preferred form of the invention a nasal mask 5 is shown, other forms of patient interface such as a nose and mouth mask or full-face mask may be used. Furthermore, while a variable speed motor is preferred, other means for providing a supply of breathable gas at positive pressure may be used, such as a constant speed motor with variable venting or a stepped-down piped pressure supply.

In accordance with the methods described in U.S. Pat. No. 5,704,345 (Berthon-Jones), the entire contents of which are hereby incorporated by cross-reference, indications of sleep disordered breathing, or airway obstruction in the patient, are monitored by the device. For example, flow, pressure and snore sensors 10, 11, 12 provide information on the shape of the inspiratory flow-time curve, patient ventilation and snore. A generally flattened inspiratory flow-time curve is taken as an indication of partial obstruction, as is the presence of snoring.

I. Obstruction Indicators (a) Shape Factors

In one form, the shape of the flow-time curve is monitored as follows. The digitized flow signal is filtered to remove any leak component. Inspiratory and expiratory portions of each breath are then identified by a zero-crossing detector. A number of evenly spaced points (typically sixty-five), representing points in time, are interpolated by an interpolator (in software) along the inspiratory flow-time curve for each breath. The curve described by the points is then scaled by a scaler to have unity length (duration/period) and unity area to remove the effects of changing respiratory rate and depth.

Conveniently, the scaled breaths are compared in a comparator (in software) with a prestored template representing a normal unobstructed breath. The template is very similar to the curve for a normal inspiratory event. Breaths deviating from this template by more than a specified threshold (typically 1 scaled unit) at any time during the inspiratory event, such as those due to coughs, sighs, swallows and hiccups, as determined by a test element, are rejected.

For data not rejected by this test, a moving average of the first such scaled point is calculated by an arithmetic processor for the preceding several inspiratory events. This is repeated over the same inspiratory events for the second such point, and so on. Thus, sixty-five scaled data points are generated by the arithmetic processor, and represent a moving average of the preceding several inspiratory events. The moving average of continuously updated values of the sixty-five points are hereinafter called the "scaled flow". Similarly, a single inspiratory event can be utilized rather than a moving average.

From the scaled flow two shape factors that directly relate to the determination of partial obstruction are calculated. Each shape factor equates to the Obstruction Index discussed above.

The first shape factor is the ratio of the mean of the middle thirty-two scaled flow points to the mean overall sixty-five scaled flow points. This is thus a determination of the reduction of the magnitude (depression) of the mid-portion of the scaled inspiratory event(s). Since the mean for all sixty-five points is unity, the division need not actually be performed.

For a normal inspiratory event this ratio will have an average value in excess of unity, because a normal inspiratory event is of higher flow in the middle than elsewhere. Conversely, for a severely flow-limited breath, the ratio will be unity or less, because flow limitation occurs particularly during the middle half of the breath when the upper airway suction collapsing pressure is maximal. A ratio of 1.17 is typically taken as the threshold value between partially obstructed and unobstructed breathing, and equates to a degree of obstruction that would permit maintenance of adequate oxygenation in a typical user.

In other embodiments the number of sampled points, number of breaths and number of middle points can be varied, and still achieve a meaningful determination of whether partial obstruction is occurring. The threshold value similarly can be a value other than 1.17. Decreasing the threshold makes the device less sensitive to detecting obstruction. Increasing the threshold makes the device more sensitive to detecting obstruction.

Alternatively, the second shape factor is calculated as the RMS deviation from unit scaled flow, taken over the middle thirty-two points. This is essentially a measure of the flatness of the midportion of the scaled respiratory event(s). For a totally flow-limited breath, the flow amplitude versus time curve would be a square wave and the RMS deviation would be zero. For a normal breath, the RMS deviation is approximately 0.2 units, and this deviation decreases as the flow limitation becomes more severe. A threshold value of 0.15 units is typically used. Decreasing the threshold makes the device less sensitive to detecting obstruction. Increasing the threshold makes the device more sensitive to obstruction.

Optionally, the shape factor may be determined by weighting certain portions of the flow signal as disclosed in U.S. patent application Ser. No. 09/924,325, filed on Aug. 8, 2001, the entire disclosure of which is hereby incorporated by reference.

Both shape factors discussed above can be utilized independently in implementing the methodology carried out by the apparatus, and result in the sensitive and reliable detection of partially obstructed breathing. Better performance again is obtained by implementing both shape factors executed by the controller so that both shape parameters act together. In this case, the second shape factor is preferred for use to detect all but the most severe obstructions, and the first shape factor therefore is preferred for detecting only the most severe obstructions, achieved by reducing the critical threshold from 1.17 to 1.0.

The two shape factors may operate in concert. The scaled flow signal is provided to a shape detector. The shape detector generates both shape factors. The first shape factor is applied to a decision block and compared against the threshold value of 1.0. If the outcome of the comparison is "Yes", then it is determined that there should be an increase in the CPAP pressure setting. The second shape factor is provided to the decision block, and a comparison made against a threshold value of 0.15. If the answer is "Yes", then it also is appropriate for an increase in the CPAP pressure.

In either case, if the result of the comparison is "No", then those results are ANDed in an AND operation. That is, an output will only be achieved if both threshold criteria are not satisfied. In this case, there is no partial obstruction, or partial obstruction has subsided, in which case it is appropriate to decrease the CPAP pressure.

This arrangement avoids any peculiarities affecting either algorithm. For example, the presence of an initial non-flow-limited period early in a breath can permit an early sharp peak in the flow-time curve. This means that the scaled flow during the middle half of the breath may be below unity. For very severely obstructed breaths, the RMS deviation from unity may therefore rise again, and the second shape factor will fail to recognize such breaths. They will, however, be correctly identified by the now desensitized first shape factor. Some normal breaths can involve an inspiratory flow-time waveform approximating a right triangle, where the mean flow during the middle half of inspiration is close to unity. Such a waveform correctly triggers neither shape factor. That is, the instantaneous flow during the middle half of the inspiration is only unity at a single point, and above or below unity elsewhere, so the RMS deviation from unit scaled flow will be large.

In one form of the invention, a new shape factor is calculated for the inspiratory portion of each breath. In another form, a shape factor is calculated from the inspiratory portion of two or more breaths. Changing the number of breaths used in the calculation of a shape factor changes the sensitivity of the device. Including fewer breaths makes the device more sensitive to indications of partial obstruction.

Once a determination has been made that there is an indication of partial obstruction, the treatment pressure may be increased. For example, when the first shape factor is below 1.0, the CPAP pressure is increased in proportion to the amount of the ratio being below 1.0. The difference between the shape factor and the threshold may be multiplied by some gain to derive the change in pressure. In one form, an increase of 1 cm $H_2O$ per breath per unit below a ratio of 1.0 is used. Conversely, if the ratio is above 1.0, indicating an absence of partial obstruction, the CPAP pressure is gradually reduced with a time constant of 20 minutes. If the second shape factor is below 0.2, the CPAP pressure is increased at a rate of 1 cm $H_2O$ per breath per unit below 0.2. Conversely, if the shape factor is above 0.2 units, the pressure is gradually lowered with a time constant of 20 minutes. The amount of the increase or decrease in pressure in the presence or absence of an indication of partial obstruction defines in part how aggressively the algorithm adapts its treatment.

Those skilled in the art will recognize that other methods for detecting flow limitation may be used, for example, by comparing a roundness index and a threshold, which may also be controlled to increase or decrease sensitivity in detection.

(b) Snore Detection

As previously mentioned, detecting snoring can be an indicator of obstruction in the patient's airway. If a snore is detected by a snore detector (such as that disclosed in U.S. Pat. No. 5,245,995, the entire contents of which are incorporated by reference), then the mask pressure is also increased. If the snore index on the given breath exceeds a critical threshold value, the pressure is increased by 1 cm $H_2O$ per unit above the threshold value.

Increasing the amount by which the pressure is increased makes the device treat more aggressively. The default threshold for the snore index is 0.2 units, corresponding approximately to a snore that can only just be reliably detected by a technician standing at the bedside. Increasing the snore threshold makes the device less sensitive. In one form of the invention, the rate of rise in pressure is limited to a maximum of 0.2 cm $H_2O$ per second, or 12 cm $H_2O$ per minute. Conversely, decreasing the snore threshold makes the device more sensitive.

II. Index of Respiratory Effort Related Arousal or Sleep Arousal

To monitor the effectiveness of the device in treating sleep disordered breathing, an index of sleep arousal or a respiratory effort related arousal is calculated. (As used in the claims at the end of this description, the term arousal index refers to a measure that is a function of the frequency of arousals, be they due to sleep arousals or respiratory effort related arousals.) In one form, the index is calculated from the size of a patient's breath. The size of a patient's breath can be determined by monitoring the flow rate of air with time and integrating to calculate volumes. If a patient exhibits a run or sequence of breaths of a first size followed by a larger breath, this is an indication that he is being aroused from sleep because of inadequate treatment and that more aggressive therapy may be required. For example, a run or sequence of 8 small breaths followed by a large breath can be an indicator that the patient is being aroused from sleep. In one form, a breath would be considered "large" if it was more than twice as large as previous breaths or small breaths. Breaths would be considered "small" if they were less than the average minute ventilation. While in a preferred form it is only necessary to monitor patient respiration, other indices of sleep arousal may be used. For example, sensors can be used that determine indications of sympathetic nervous system activity such as sweating and heart rate.

Figure 4:
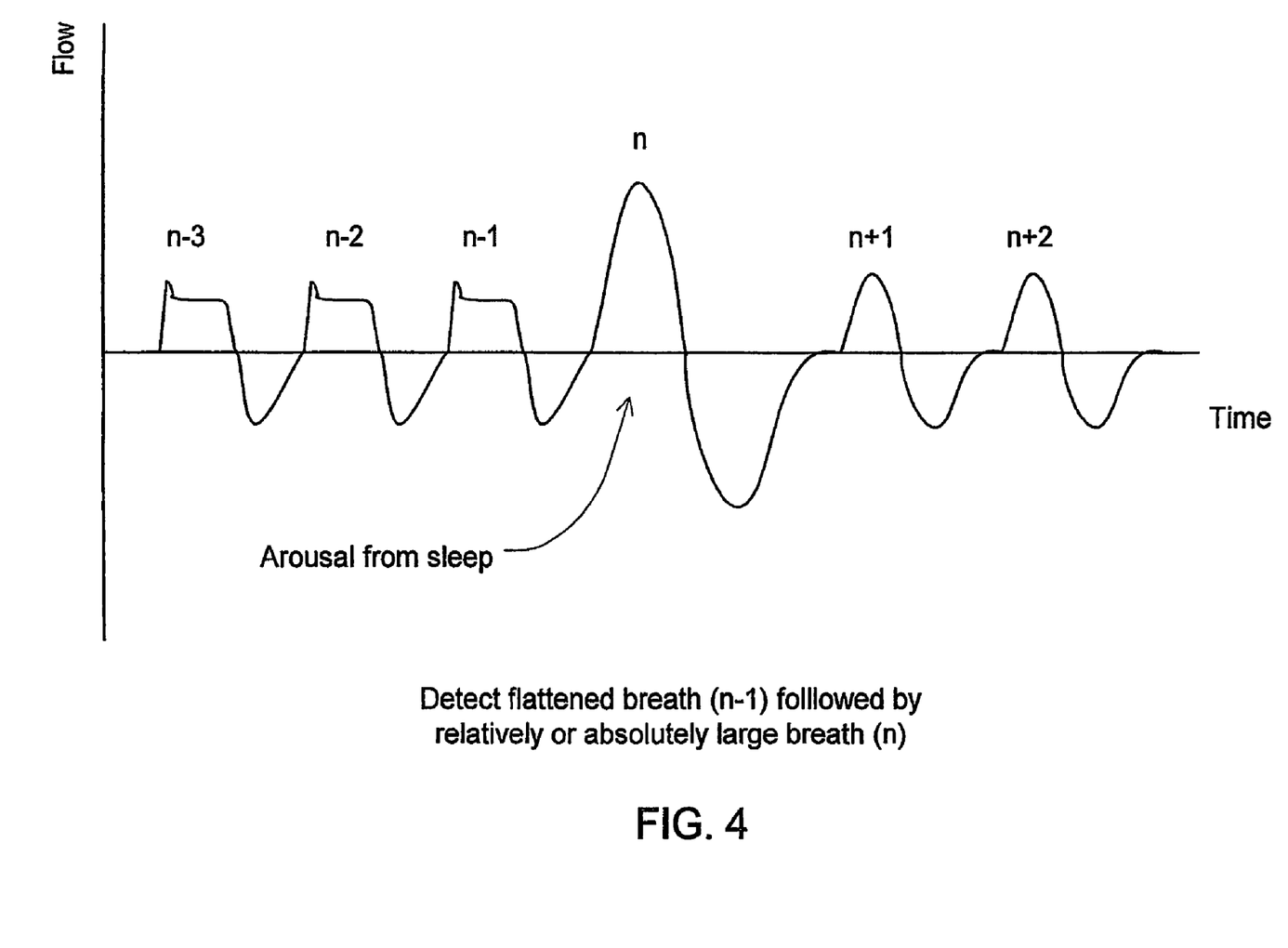
FIG. 4 is a graph of a flow versus time curve illustrating an event of sleep arousal.

In an alternative embodiment, arousal from sleep may be determined by detecting a post apnea sigh or yawn. This may be accomplished by a CPAP apparatus. For example, respiratory airflow is monitored to detect a breathing sequence including a degree of flattening or obstruction in a breath followed by a large breath. The flattening or obstruction may be, for example, a minor or subtle degree of flattening that might not even be considered sufficient to increase the CPAP pressure, and may be detected using the shape factors previously described with a very sensitive threshold. The "large" breath may be considered "large" if it is absolutely a large breath of a predetermined quantity or more simply if it is relatively larger than other breaths of the patient such as one or more of those immediately preceding the large breath, which may be determined from volume. For example, the inspiratory portion or a respiratory airflow signal may be integrated on a breath by breath basis. A detectable condition of this type is illustrated in FIG. 4. In the figure, the detection of sleep arousal may be based on the detection of breath n following the flow limited breath n-1 or several such breaths n-1, n-2 and n-3.

In one embodiment of the invention, the detection of a respiratory effort related arousal may be estimated by examining respiratory irregularities with a short term moving average measure of ventilation from data or a signal from the flow sensor. Peaks or other significant or relative increases in the measure are indicative of arousal events. The short term moving average can be determined by integrating a low pass filtered respiratory airflow signal with a time constant chosen for this purpose.

III. Overall Control Based on Sleep Arousal Detection

Figure 2:
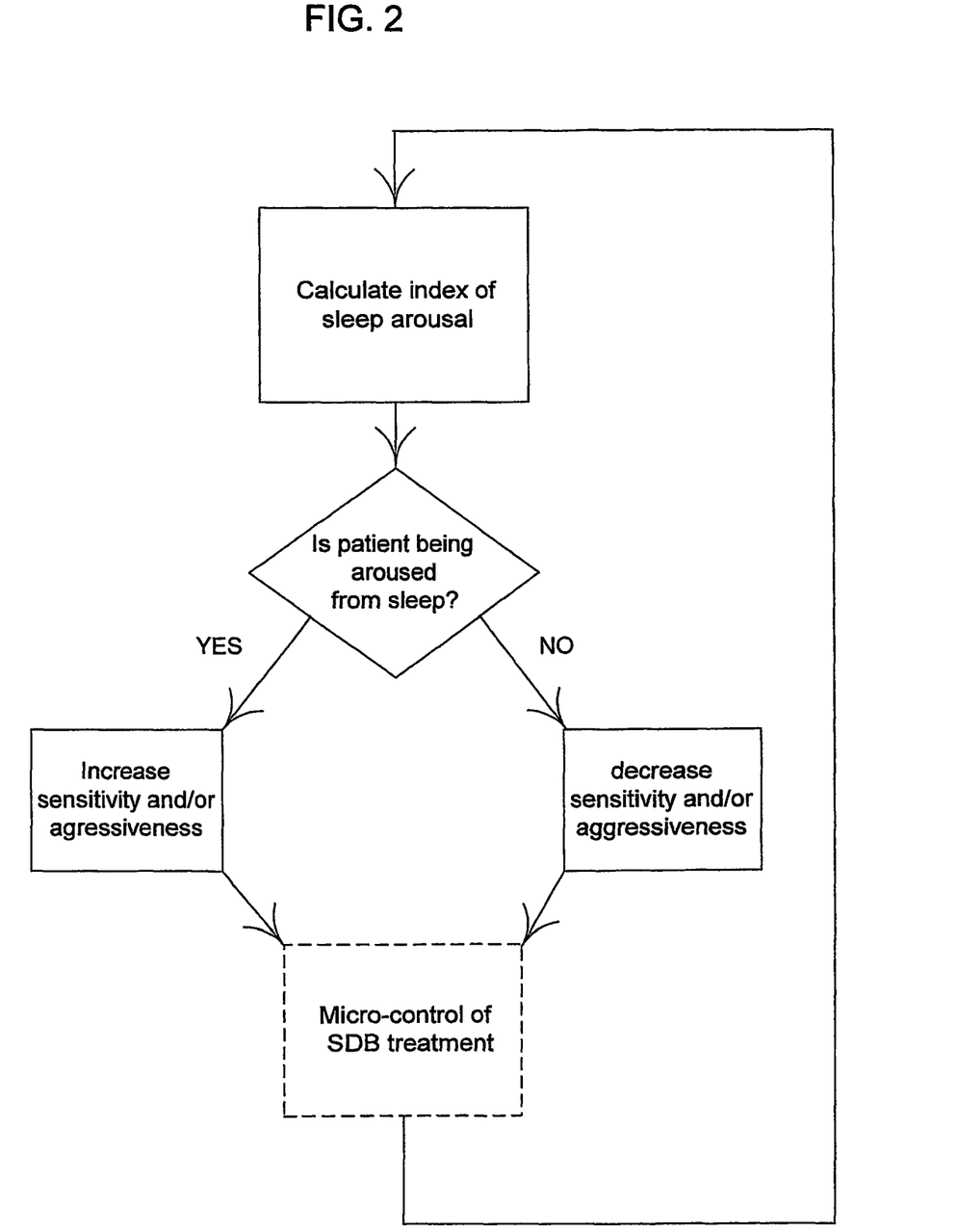
FIG. 2 shows a "macro-control" algorithm in accordance with an embodiment of the invention.
Figure 3:
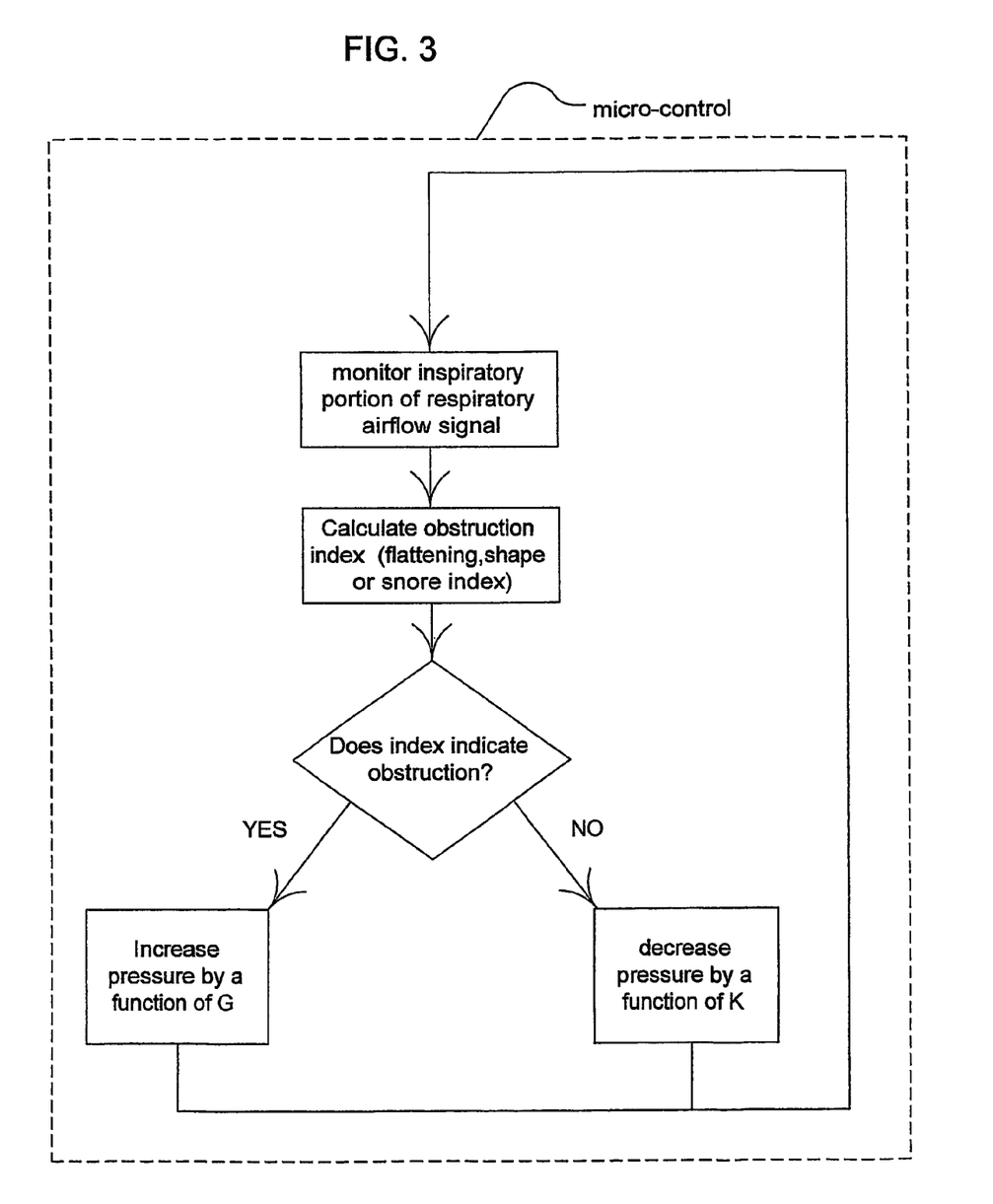
FIG. 3 shows a "micro-control" algorithm in accordance with an embodiment of the invention.

An overall or "macro-control" algorithm in accordance with the invention makes a determination of how aggressively to treat the patient based on a determination of whether he is being successfully treated, and then adjusts the parameter values of the "micro-control" loop accordingly. The macro-control loop is shown in FIG. 2 and the micro-control loop is shown in FIG. 3, where the latter is part of the former, as indicated. (The functions of G and K shown at the bottom of FIG. 3 are discussed in connection with FIGS. 7 and 8 below.) Patients who are becoming aroused from sleep are treated more aggressively. Patients who are not being aroused from sleep are treated less aggressively. Similarly, based on the assessment of the success of the treatment, the algorithm can adjust the sensitivity of the obstruction detection routine to increase sensitivity for less successful treatment.

In one form of the invention, the device starts treating the patient using default settings for parameter values, for example, a threshold value, but monitors sleep arousal during the course of the night. At the end of the night's treatment, representative parameter values are stored in a memory and on subsequent treatment nights, the representative parameter values from the previous treatment session are used at the beginning of treatment.

If a determination that the patient is being aroused from sleep has been made, the number of breaths which are averaged to determine a shape index is reduced. If that is insufficient to achieve an improvement in the patient, then the threshold level necessary to initiate an increase in treatment pressure is adjusted, making the device more sensitive.

In another form, the time constant of decay of treatment pressure is increased if treatment is determined to be ineffective based on the arousal index. In this way, the pressure stays high for a longer period of time following an increase which has resulted from the detection of an indication of partial obstruction.

Optionally, the apparatus may be configured to increase the treatment pressure in response to the detection of an event of sleep arousal or respiratory effort related arousal in accordance with one of the previously described arousal indices. For example, pressure may be increased by a certain unit of pressure for each detected event of arousal up to a maximum pressure. Similarly, the pressure may be reduced towards a minimum support pressure in the absence of arousal events over a period of time, such as one hour. As an alternative, data associated with one or more breathing cycles immediately preceding the breath indicative of the sleep arousal may be subsequently analyzed by the apparatus to determine a proportional amount of treatment pressure change that would be appropriate to compensate for the respiratory related event. Thus, additional or supplemental analysis may be triggered by the detection of the sleep arousal. For example, the prior breaths may be re-analyzed by one of the shape factors or obstruction detectors discussed above with thresholds of greater sensitivity than they were previously subjected to as discussed herein. With the new analysis, a calculated proportional amount of pressure change may be generated based on the detection of the flow limitation if such flow limitation had not previously been detected for the particular breath. In this embodiment, flow signal related data from previous breaths can be stored in memory for the re-analysis.

In one embodiment of the invention, the control methodology defaults to keep the pressure low (4 cm H$_2$O) while the patient is awake but will increase pressure with sleep onset. Methods for doing so are known in the art. The device then detects the presence of respiratory related event arousals or sleep arousals preferably after a period of time over which the patient may fall asleep. In one form the device will then monitor flow to detect a short, sudden period of flow limitation, terminated by a big breath, which will be indicative of a respiratory arousal. If it detects such a sleep arousal, it will become (1) more sensitive to detecting obstructive or other SDB events, for example, by making adjustments to detection thresholds, (2) more rapid or aggressive in its pressure response to these events, for example, by increasing the pressure gain used in response to each event, and (3) more reluctant to again lower the pressure when arousal events have stabilized or discontinue.

For subsequent sleep arousals (representing patients intermediate between the stable and unstable ends of the spectrum), the above process is repeated, so that after about two arousals or some near number, the device will adjust itself to treat with greatly increased rate of response, and once an optimal pressure is found, to maintain that optimal pressure for an hour or so.

Preferably, if further respiratory arousals are detected (representing the most unstable, arousable, currently poorly treated extreme of the spectrum) the device remains indefinitely at a therapeutic pressure. Thus, the device would have become essentially a fixed CPAP device, with automatic detection of sleep onset. Optionally, in the next day of treatment, the device can revert either to its default behavior as previously described, or it can resume to a larger or smaller degree the sensitivity of detection, aggressiveness (more rapid) treatment pressure response, or persistence in maintaining a higher pressure by using the settings arrived at during the prior session.

Figure 5:
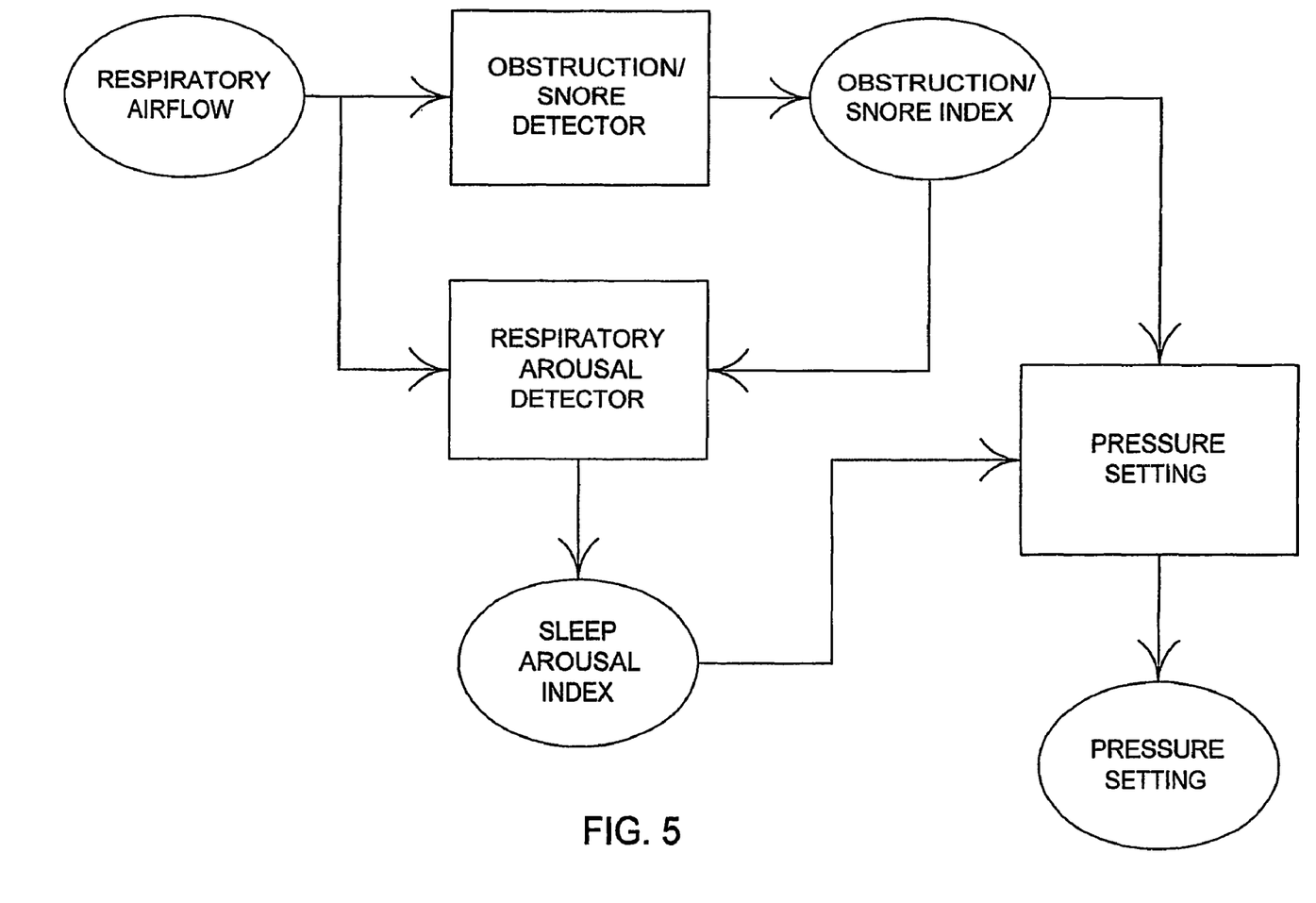
FIG. 5 is a chart of information flow in one embodiment of a device for adjusting settings of a pressure delivery device in accordance with a function of sleep or respiratory arousal.
Figure 6:
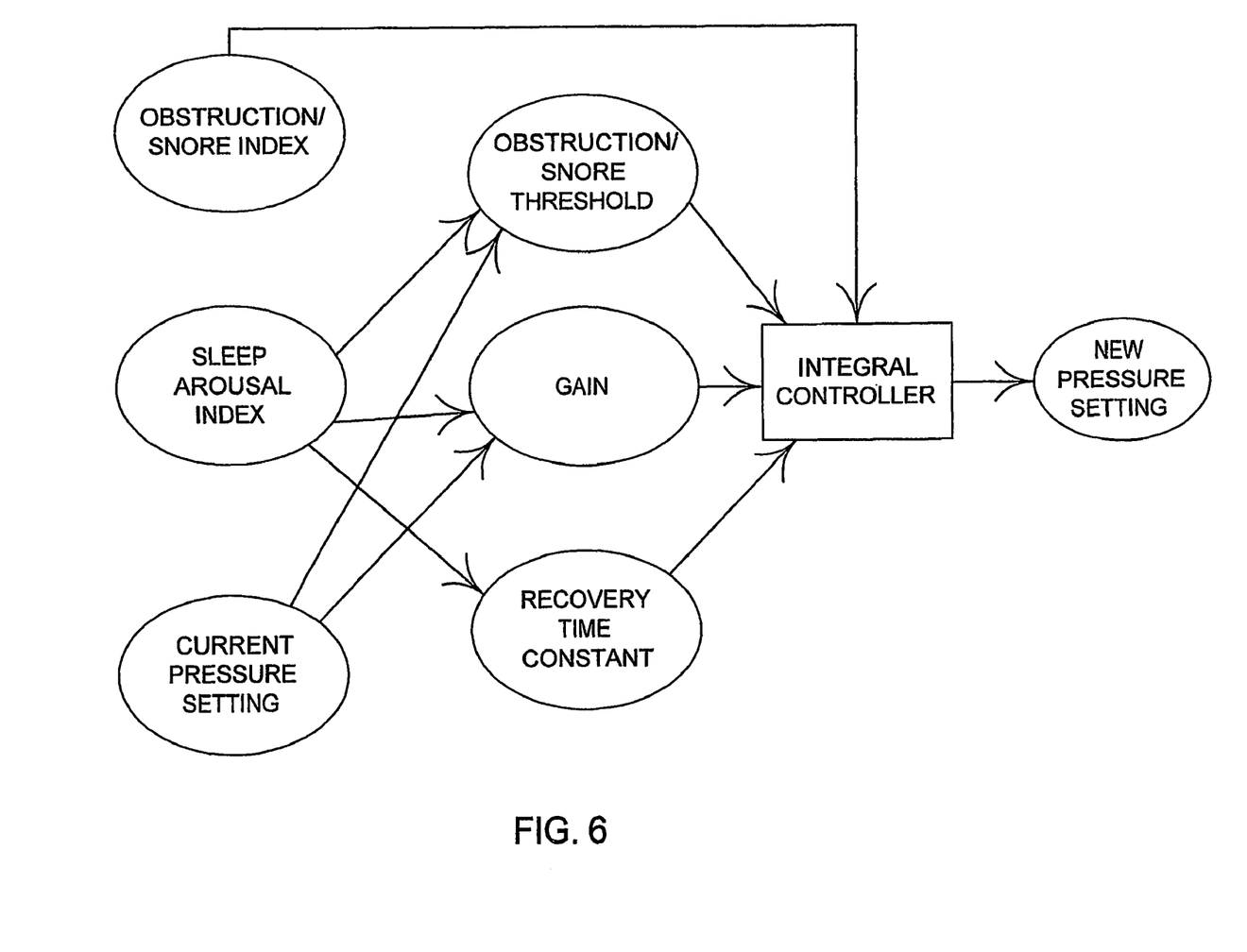
FIG. 6 illustrates one embodiment of the input of a controller for adjusting treatment pressure based on a sleep arousal index.

A methodology/apparatus for sleep arousal-based control in the treatment of SDB is illustrated in FIGS. 5 and 6. As shown in FIG. 5, an obstruction and/or a snore detector derive an obstruction index and/or a snore index from respiratory airflow. (As used in the claims, the term obstruction detection embraces detection of a high obstruction index, a high snore index, or both.) A respiratory effort related arousal or sleep arousal detector derives a sleep arousal index from an obstruction index or snore index and respiratory airflow. The obstruction and/or snore index and the sleep arousal index are then utilized in deriving a pressure setting by a pressure determination device. FIG. 6 depicts the pressure determination device of FIG. 5. As depicted in FIG. 6, the respiratory effort related arousal/sleep arousal index is applied to adjust the thresholds compared with the obstruction/snore indices. The sleep arousal index is also applied to adjust the gain to change the aggressiveness of pressure increases. Finally, the sleep arousal index is also applied to adjust the recovery time constant of the treatment pressure to delay the pressure decay after an SDB event has subsided. In other words, a higher respiratory arousal index renders a more sensitive obstruction/snore detection, a more aggressive pressure increase in response to detected events and a prolonged period of pressure treatment to an SDB event.

(a) Sleep Arousal Based Gain Adjustment

As previously noted, in response to detected sleep arousal(s), the pressure response made to detected SDB events may be modified to generate more aggressive increases and/or less aggressive decreases in pressure. Various functions can provide these adjustments as a function of an index of detected sleep arousals. For example, the aggressiveness of pressure withdrawal (i.e., a less aggressive decrease) can be accomplished with the following formula, which may serve as the pressure change when there is no detected obstruction that would require an increase in pressure.

$$\Delta P = -K(P - P_{min}) \text{ when } S > S_T$$

where:
- $\Delta P$ is the pressure adjustment or the pressure change;
- K is a function of the detected sleep arousal;
- P is the actual pressure being delivered to the patient;
- $P_{min}$ is a desired minimum pressure level;
- S is an obstruction index such as flow flattening or snore index;
- $S_T$ is a threshold value for the obstruction index.

Figure 7:
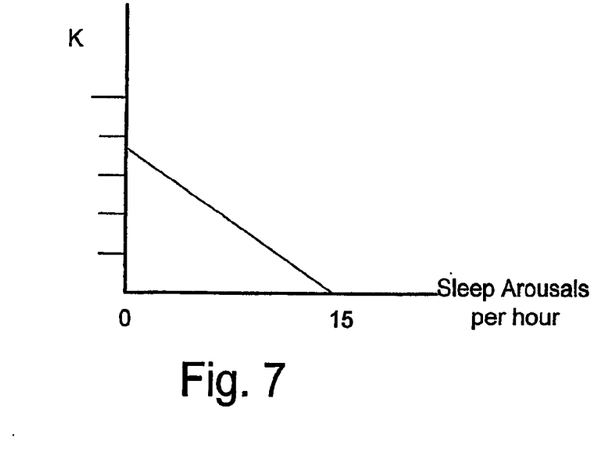
FIG. 7 depicts a function for adjusting the aggressiveness of reductions in treatment pressure in accordance the measure of sleep arousal.

Various functions of sleep arousal K may be devised. For example, one such function may be based on the number of detected sleep arousals with K decreasing with an increasing number of detected events to a maximum. Such a function is illustrated in FIG. 7. The selection of the number of arousals and maximum value of K may be based on clinical experimentation and would be within the skills of individuals in the field. As shown, the number of arousals may be based on a function of time, for example, a per hour basis using the number of events from the immediately preceding hour. In an alternative embodiment, the function may be based on the number of sleep arousals in a particular session with the device, for example, during a single night. In the example formula shown, as the pressure decreases after obstruction is no longer found, pressure will decrease more slowly as the number of sleep arousals detected approaches 15 events in the previous hour. Thus, the decay in treatment pressure as a result of the above function will tend to be exponential, approaching the minimum pressure for few or no detected events but decaying less rapidly as a greater number of events are detected. As shown, exceeding a certain number of such detections can prevent the device from withdrawing treatment as K approaches 0 near a chosen critical number of sleep arousal events.

Conversely, when the shape detector/snore index indicates that there is an SDB event that must be treated by comparing a detected index to a threshold, the treatment pressure will be increased as a function of some gain. In one embodiment of the invention, the gain affecting the rate of the pressure increase is a function of sleep arousal. One such gain may be utilized to deliver treatment pressure in accordance with the following formula:

$$\Delta P = G(S - S_T) \text{ when } S < S_T$$

where
 $\Delta P$ is the pressure adjustment or the pressure change;
 G is a function of the detected sleep arousal;
 S is an obstruction index such as flow flattening or snore index;
 $S_T$ is a threshold value for the obstruction index.

Figure 8:
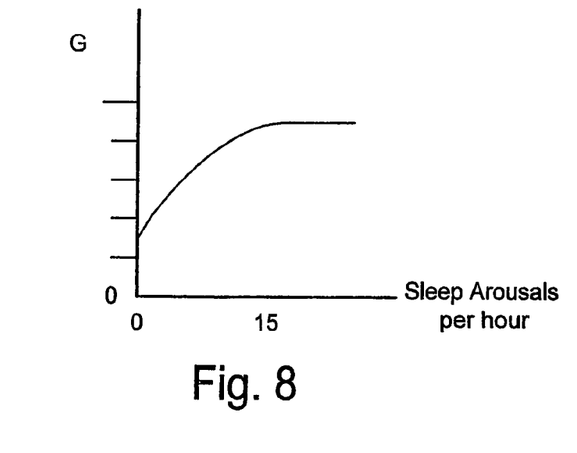
FIG. 8 depicts a function for adjusting the aggressiveness of increases in treatment pressure in accordance the measure of sleep arousal.

For example, an exponential function for G may be utilized to increase the gain as an increasing function of a cumulative number of detected sleep arousal events. One such function is illustrated in the graph of FIG. 8. In the graph shown, if no events of sleep arousal are detected or if none are detected after a certain period of time, for example, none in the immediately preceding hour, the gain remains at a typical gain. However, as the number of these detected events accumulates, the gain will be increased, preferably as an exponential function approaching some maximum or higher gain. Of course, as the number of detected sleep arousal events decreases, the gain will be reduced according to the chosen graph of the sleep arousal function.

While an exponential function is shown, those skilled in the art will recognize that other functions for increasing the gain as a function of an increasing number of detected sleep arousal events can be utilized, for example, a linear or other ramp function.

(b) Sleep Arousal Based Threshold Adjustment

Figure 9:
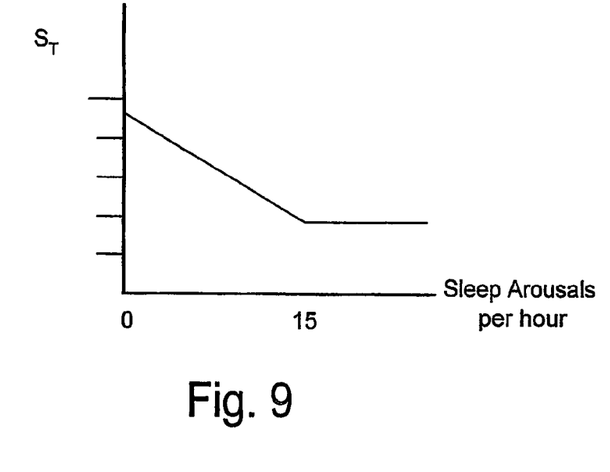
FIG. 9 depicts a function for adjusting the sensitivity of flow limitation detection in accordance with the measure of sleep arousal.
Figure 10:
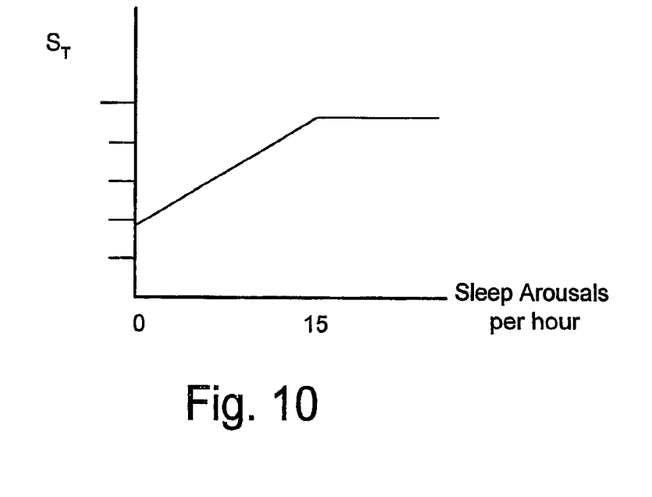
FIG. 10 illustrates another function for adjusting the sensitivity of flow limitation detection in accordance with the measure of sleep arousal.

As previously mentioned, an adjustment or change to the sensitivity of the apparatus may be implemented by changing obstruction response thresholds as a function of an index of sleep arousals. Those skilled in the art will recognize that a change by either an increase or decrease in the threshold amount may be associated with either an increase or decrease in sensitivity. This relationship is attributable to the nature of the particular obstruction index and its threshold as described previously. Some suitable functions relating to the methods disclosed herein are illustrated in the graphs of FIGS. 9 and 10. In the illustrated exemplary graph of FIG. 9, as the number of detected events increases over a period of time, such as the immediately preceding hour, the threshold will be a decreasing function, such as a ramp, from a less sensitive to a more sensitive value. For example, for adjustment to the snore threshold as discussed above, when no sleep arousal events are detected, the snore threshold may remain at its default of about 0.2 units. However, as the number of arousal events increases, the threshold may be reduced according to a ramp or linear function to a lower threshold, rendering the detection of snoring related obstructive events more likely (increasing sensitivity).

The sample graph of FIG. 10 may be utilized to adjust or change the sensitivity of the shape factors discussed previously. As illustrated, a default threshold may remain constant in the absence of detected sleep arousal events. However, as the detected number of sleep arousals increases, the shape factor threshold will increase rendering the detection of obstructive events more likely (more sensitive), which in turn will result in a greater likelihood of an increase in pressure treatment to address the detected obstruction events. Those skilled in the art will recognize that other functions of the sleep arousal index may be utilized to change the sensitivity of various obstruction thresholds.

Figure 11:
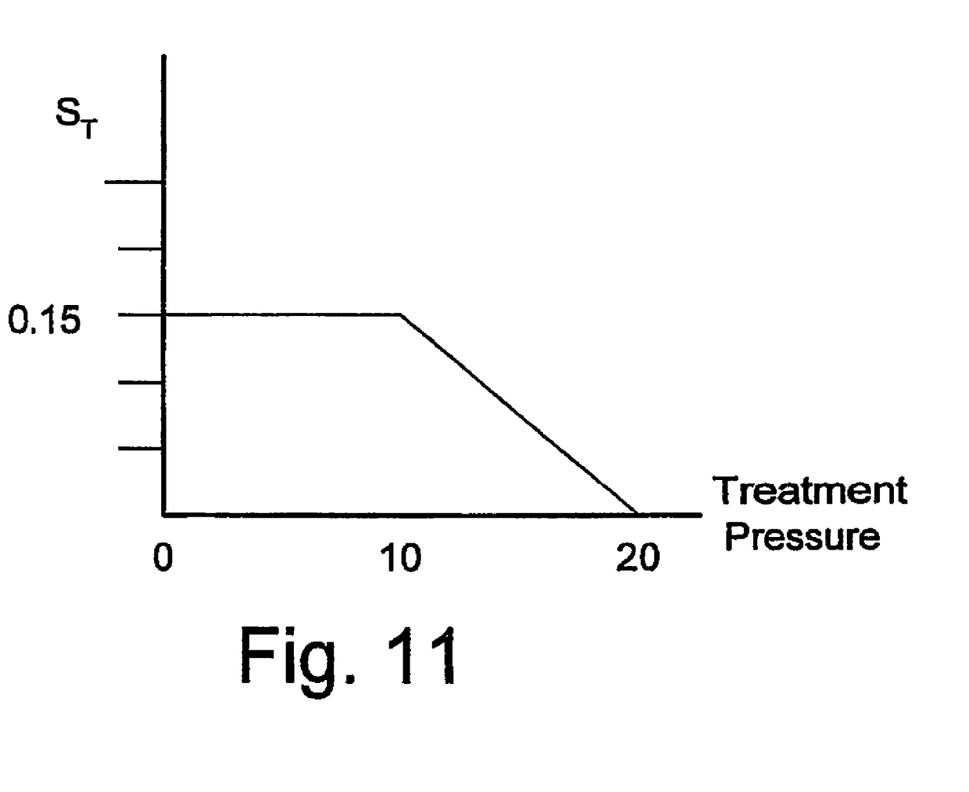
FIG. 11 depicts a function for adjusting the sensitivity of flow limitation detection in accordance with the measure of treatment pressure.

Similarly, the threshold may also be a function of treatment pressure. One such function is illustrated in FIG. 11 as it relates to the second shape factor discussed previously. In the example, the threshold is held at a default value of 0.15 until the treatment pressure exceeds 10 cm $H_2O$. The threshold then decreases, approaching 0 as the treatment pressure approaches 20 cm $H_2O$.

In another form of the invention, apparatus for treating sleep disordered breathing is provided with a controller programmed to select the most appropriate therapy from a "toolbox" of treatment algorithms. The controller has two parts.

A first part is programmed to provide different forms of therapy, for example, basic CPAP, automatically adjusting CPAP (such as described in U.S. Pat. No. 5,704,345), bi-level CPAP or more complicated therapies such as for treatment of Cheyne-Stokes (CS) respiration (see, for example, U.S. Pat. No. 6,532,959, the contents of which are hereby expressly incorporated by cross-reference).

The second part monitors the patient and the effectiveness of the current treatment algorithm. Thus a device in accordance with the invention includes an apnea monitor able to distinguish central and obstructive apneas (see, for example, U.S. Pat. No. 5,704,345), an oximeter able to detect oxygen desaturation events, and a snoring monitor. Indices are calculated. For example, the controller determines the number of central apneas, obstructive apneas, hypopneas, and desaturation events and determines appropriate indices such as the Apnea Hypopnea Index (AHI), Central apnea Index (CI) and desaturation index (DI). The intensity and severity of snoring is also monitored, as is flow flattening.

The controller changes treatment modes when a particular mode is indicated. In one form, the device defaults to basic CPAP treatment at a pressure suitable for treating a range of conditions such as 8-12 cmH$_2$O, preferably 9 cmH$_2$O. Snoring, flow flattening and obstructive apneas indicate that the treatment level may be insufficient and the device will switch to an automatic CPAP treatment algorithm (see U.S. Pat. No. 5,704,345). However, an AHI>5/hour is indicative that the sensitivity of the Automatic CPAP algorithm needs to be increased, and the controller will then attempt this. A CI>5/hour is indicative that a bi-level CPAP or Cheyne-Stokes treatment algorithm is appropriate. If AHI+CI>5/hour then bi-level or CS treatment is indicated. Ongoing periodic desaturations (for example, 3% 4% desaturation>10/hour) indicate bi-level CPAP.

In one form of the invention, a central apnea detector is included. This can then be used to monitor the occurrence of central apneas in Congestive Heart Failure (CHF). By monitoring central apneas, progression of the disease can be monitored. An alarm or device message could be used to alert a physician of disease progression. Furthermore, in as much as a central apnea marks the onset of decompensation, the invention can be used to provide a warning of acute decompensation and the requirement of hospitalization.

While the invention has been described with various alternative embodiments and features, it is to be understood that the embodiments and features are merely illustrative of the principles of the invention. Those skilled in the art would understand that other variations can be made without departing with the spirit and scope of the invention.

We claim:

1. A method for treating sleep disordered breathing by controlling a machine to apply breathable gas at positive pressure to the airway of a patient comprising the steps of:
   determining the patient's arousal index for use in an outer loop of a control algorithm, the arousal index being calculated from a size of the patient's breath and being a measure of the frequency of sleep arousals,
   monitoring the patient's respiratory airflow signal in an inner loop of said control algorithm to detect an airway obstruction,
   said control algorithm being used to adjust the positive pressure applied by said machine,
   if said arousal index is above a particular threshold, then increasing the sensitivity of detection of the obstruction and/or the aggressiveness of the treatment, and
   if the arousal index is below a particular threshold, then decreasing the sensitivity of detection of the obstruction and/or the aggressiveness of the treatment,
   wherein said arousal index is determined to be high by monitoring a flow rate over a sequence of breaths and checking whether the sequence is followed by a large breath.

2. A method for treating sleep disordered breathing in accordance with claim 1 wherein a patient's breath is considered to be large if it is twice as large as previous breaths.

3. A method for treating sleep disordered breathing in accordance with claim 1 wherein a sleep arousal is determined by a Continuous Positive Airway Pressure (CPAP) apparatus detecting a post apnea sigh or yawn.

4. A method for treating sleep disordered breathing in accordance with claim 1 wherein obstruction detection is a function of average airflow shape and the sensitivity of obstruction detection is increased by reducing a number of breaths in the average.

5. A method for treating sleep disordered breathing in accordance with claim 4 wherein if increasing the sensitivity of obstruction detection does not improve the patient's condition, then a threshold level necessary to increase the treatment pressure in the inner loop is adjusted to make it more sensitive.

6. A method for treating sleep disordered breathing in accordance with claim 1 wherein a threshold level necessary to increase a treatment pressure in the inner loop is adjusted in order to change the sensitivity of obstruction detection.

7. A method for treating sleep disordered breathing in accordance with claim 1 wherein a time constant of decay of a treatment pressure in the inner loop is increased in order to increase aggressiveness of treatment.

8. A method for treating sleep disordered breathing in accordance with claim 1 wherein incremental changes in a treatment pressure in the inner loop are increased in order to increase aggressiveness of treatment.

9. An apparatus for treating sleep disordered breathing comprising:
   a controller for (a) determining a patient's arousal index for use in an outer loop of a control algorithm, the arousal index being calculated by said controller from the size of a patient's breath and being a measure of the frequency of sleep arousals, and (b) monitoring the patient's respiratory airflow signal in an inner loop of said control algorithm to detect an airway obstruction, and
   means responsive to said arousal index being above a particular threshold for increasing the sensitivity of the obstruction detection and/or the aggressiveness of the treatment, and responsive to said arousal index being below a particular threshold for decreasing the sensitivity of the obstruction detection and/or the aggressiveness of the treatment, wherein said controller determines the arousal index to be high by monitoring a flow rate over a sequence of breaths and checking whether the sequence is followed by a large breath.

10. An apparatus for treating sleep disordered breathing in accordance with claim 9 wherein said controller considers a patient's breath to be large if it is twice as large as previous breaths.

11. Apparatus for treating sleep disordered breathing in accordance with claim 9 wherein said controller uses a Continuous Positive Airway Pressure (CPAP) apparatus to determine a sleep arousal by detecting a post apnea sigh or yawn.

12. Apparatus for treating sleep disordered breathing in accordance with claim 9 wherein said controller detects an obstruction as a function of average airflow shape and increases the sensitivity of obstruction detection by reducing a number of breaths in the average.

13. Apparatus for treating sleep disordered breathing in accordance with claim 12 wherein if increasing the sensitivity of obstruction detection does not improve the patient's condition, then the controller adjusts a threshold level necessary to increase the treatment pressure in the inner loop to make it more sensitive.

14. Apparatus for treating sleep disordered breathing in accordance with claim 9 wherein said controller adjusts a threshold level necessary to increase a treatment pressure in the inner loop in order to change the sensitivity of obstruction detection.

15. Apparatus for treating sleep disordered breathing in accordance with claim 9 wherein said controller increases a time constant of decay of a treatment pressure in the inner loop in order to increase aggressiveness of treatment.

16. Apparatus for treating sleep disordered breathing in accordance with claim 9 wherein said controller increases incremental changes in a treatment pressure in the inner loop in order to increase aggressiveness of treatment.

* * * * *